United States Patent [19]

Decker et al.

[11] 4,190,601

[45] Feb. 26, 1980

[54] PRODUCTION OF TERTIARY AMINES BY REDUCTIVE ALKYLATION

[75] Inventors: Quintin W. Decker, St. Albans; Erich Marcus, Charleston, both of W. Va.

[73] Assignee: Union Carbide Corporation, New York, N.Y.

[21] Appl. No.: 911,096

[22] Filed: May 31, 1978

[51] Int. Cl.$^2$ ............................................. C07C 85/08
[52] U.S. Cl. ........................... 260/583 R; 260/563 R; 260/563 C; 260/570.8 R; 260/570.9; 260/584 R
[58] Field of Search ........ 260/583 R, 563 R, 570.8 R, 260/563 C, 584 R, 570.9

[56] References Cited

U.S. PATENT DOCUMENTS

| | | | |
|---|---|---|---|
| 2,422,013 | 6/1947 | Haury et al. | 260/583 R X |
| 3,223,734 | 12/1965 | Fallstad et al. | 260/583 R |
| 3,366,687 | 1/1968 | Ellis et al. | 260/583 R |
| 3,394,187 | 7/1968 | Markiewitz | 260/583 R |
| 3,565,954 | 2/1971 | Bouniot | 260/563 |
| 3,976,697 | 8/1976 | Kuntschik et al. | 260/583 |

OTHER PUBLICATIONS

Fieser et al., "Reagents for Organic Synthesis", vol. 1, pp. 353-354 (1967).
Ginsburg, "Concerning Amines", pp. 33-38 (1967).

*Primary Examiner*—John Doll
*Attorney, Agent, or Firm*—Franklyn Schoenberg

[57] ABSTRACT

A process for the reductive alkylation of secondary amines with either aliphatic aldehydes or aliphatic ketones in contact with hydrogen, a water-segregating agent and a hydrogenation catalyst to form tertiary amines.

15 Claims, No Drawings

PRODUCTION OF TERTIARY AMINES BY REDUCTIVE ALKYLATION

BACKGROUND OF THE INVENTION

Tertiary amines, alone or mixed with other materials, are widely used in many areas. Known applications for tertiary amines are as fungicides, bactericides, surfactants, ganglionic blocking agents, rust inhibitors, antioxidants, surface modifiers for textiles, metal complexing agents, viscosity stabilizers, hypergolic fuels, solvents, pH stabilizers, color stabilizers, and as catalysts in a large variety of reactions such as curing of epoxide resins.

The production of tertiary amines by reductive alkylation of secondary amines with aldehydes has been known for at least 50 years. Yields have ranged from several percent to 100 percent. The best alkylations are obtained using formaldehyde as the alkylating agent and platinum as the catalyst. However, lower yields of tertiary amines are obtained when one employs the higher aliphatic aldehydes and/or the secondary amines with branching.

The reaction of secondary amines with ketones is more difficult and is known to give lower yields, especially as the ketone increases in size or if the ketone or secondary amine contains substituents. Thus, dimethyl ketone is generally the preferred ketone as it is the most reactive. As one or more of the methyl groups attached to the carbonyl group are replaced by larger alkyl groups, or by other groups, the yield of tertiary amine decreases. This decrease in yield is more pronounced as the size of the groups attached to the ketonic carbonyl group increases. It is also known that the presence of substituent groups on the carbon atoms alpha to the carbonyl carbon of the ketone or on the carbon atom alpha to the nitrogen atom of the secondary amine will also cause a drop in the yield of tertiary amine. In U.S. Pat. No. 2,388,807 ketones were found to be either inactive or not as reactive as aldehydes in the formation of tertiary amines, either in acid, or alkaline media, even under drastic reaction conditions.

Two side reactions can occur during the reductive alkylation of an amine with an aldehyde or ketone: (1) hydrogenation of the carbonyl group to an alcohol which negates the use of the aldehyde or ketone as an alkylating agent and (2) aldolization of the carbonyl group by the amine which leads to high molecular weight products rather than the desired tertiary amine. Another problem encountered is the difficulty of product isolation due to the proximity of boiling points of many secondary and tertiary amines. Separation of these compounds in order to obtain a pure tertiary amine is extremely difficult and complicated necessitating the use of costly separation procedures.

A method for the production of tertiary amines from secondary amines and aldehydes or ketones, such as the one hereinafter described, which would greatly increase yields of tertiary amine while minimizing the formation of tarry residues and by-products is of great importance.

SUMMARY OF THE INVENTION

It has now been found that tertiary amines can be produced by a process comprising the reductive alkylation of secondary amines with aliphatic aldehydes or aliphatic ketones in contact with hydrogen, a water-segregating agent and a hydrogenation catalyst under conditions hereinafter defined. This novel process results in much improved yields of tertiary amines from secondary amines and minimal formation of residues and by-products and allows the use of inexpensive and uncomplicated procedures to separate the product.

DESCRIPTION OF THE INVENTION

In the process of this invention secondary amines are reductively alkylated with aldehydes or ketones in contact with hydrogen, a hydrogenation catalyst and certain water-segregating agents. The aldehydes or ketones can be monofunctional or polyfunctional.

The reaction that occurs can be illustrated by the following equation in which a monoketone is used:

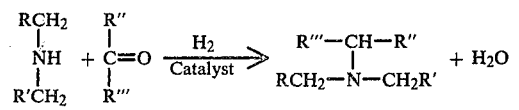

where R and R' can be:

(a) alkyl, substituted or unsubstituted, linear or branched, having from one to twenty carbon atoms, preferably from one to eight carbon atoms, such as methyl, propyl, isopropyl, butyl, sec.-butyl, octyl, undecyl, pentadecyl, eicosyl and the like;

or (b) a substituted or unsubstituted cycloalkyl having from four to eight ring carbon atoms, such as cyclopentyl, cyclohexyl, 2-methylcyclohexyl, cyclooctyl and the like;

or (c) a substituted or unsubstituted hydroxyalkyl, linear or branched, having from one to twenty carbon atoms preferably from one to eight carbon atoms, such as, hydroxymethyl, hydroxybutyl, hydroxyoctyl, hydroxydecyl, hydroxyeicosyl and the like;

or (d) a substituted or unsubstituted aralkyl having from seven to twenty carbon atoms preferably from seven to twelve carbon atoms, such as, benzyl, phenethyl, 4-methylbenzyl and the like;

or (e) hydrogen;

and R'' and R''' singly can be:

(a) alkyl, substituted or unsubstituted linear or branched, having from one to twenty carbon atoms, preferably from one to eight carbon atoms, such as methyl, isopropyl, hexyl, octyl, decyl, eicosyl and the like;

or (b) hydrogen;

or (c) when taken together they can be alkylene having from three to six carbon atoms, such as, trimethylene, tetramethylene, pentamethylene, and the like forming a cyclic ketone such as cyclobutanone, cyclopentanone, cyclohexanone and the like.

Illustrative of secondary amines suitable for use in this invention one can name, diethylamine, methylhexylamine, ethylbenzylamine, ethylpropylamine, bis(3-hydroxypropyl)amine, dibutylamine, ethylpentylamine, methyloctylamine, diheptylamine, methyl cyclopentylamine, and bis(2-hydroxyethyl)amine.

Illustrative of aldehydes suitable for use in this invention one can name formaldehyde, acetaldehyde, propionaldehyde, n-butyraldehyde, undecanaldehyde, 2-ethylbutyraldehyde, hexanaldehyde, valeraldehyde, glutaraldehyde, succinaldehyde and adipaldehyde.

Illustrative of ketones suitable for use in this invention one can name acetone, methyl ethyl ketone, 1,3-diphenyl-2-propanone, methyl isobutyl ketone, methyl methoxybutyl ketone, dipropyl ketone, methyl pentyl ketone, ethylhexyl ketone, acetylacetone, and 2,5-heptanedione.

The R, R', R" and R''' groups can be unsubstituted or substituted with any substituent group which will not unduly interfere with the reductive alkylation process of this invention. Thus, there can be present as substituent groups hydroxyl, ether linkages, silane groups ($R_3Si$), or heterocyclic rings containing oxygen atoms in the ring that are known to be essentially noninterfering. In some instances one can also have present acetyl, phenyl, ester, carboxyl, halogen, mercapto or thio groups; however, under certain reaction conditions these may interfere with the reaction or poison the catalyst. When present in the molecule, the reaction conditions must be carefully adjusted, a fact known to those skilled in the art.

Any of the known hydrogenation catalysts can be used. Illustrative thereof one can mention Raney nickel, nickel-on-kieselguhr, copper chromite, and nickel, palladium, platinum and other platinum metals such as ruthenium, rhodium, osmium and iridium deposited on inert supports such as carbon, silica and other refractory oxides. The preferred catalyst is Raney nickel. The concentration of hydrogenation catalyst can vary from about 0.5 weight percent to 10 weight percent, preferably from about 3 weight percent to 6 weight percent, based on the total weight of the aldehyde or ketone, secondary amine and water-segregating agent charged. Further, as known, the pretreatment of catalyst to remove impurities and traces of water is beneficial. Those skilled in the art of catalysis are fully familiar with the many problems encountered and precautions to be taken when working with hydrogenation catalysts.

Also present in the reaction mixture, as previously indicated, is a water-segregating agent. A water-segregating agent is defined as a compound which facilitates the removal of water during the reaction sequence. This agent is present at a concentration of from about 0.05 weight percent to 30 weight percent, preferably from about 0.1 weight percent to 20 weight percent of the total weight of the reaction mixture. Illustrative of suitable water-segregating agents one can mention the zeolitic molecular sieves, calcium chloride, magnesium sulfate, calcium sulfate, sodium sulfate, and the like. Illustrative of the preferred water-segregating agent are the Type A zeolitic hydrophilic molecular sieves which have pore diameters of from 2.5 to 5 Angstrom units, preferably from 3 to 4 Angstrom units. The water-segregating agent may be introduced in either crystalline, extrusion, powder or other form. The water-segregating agent is believed to absorb the water formed from the reaction and to hold the water tightly during the hydrogenation to prevent hydrolysis thereby permitting higher rates and yield.

The pH of the reaction mixture also has an effect on the rate of hydrogenation. It was observed that potassium carbonate, a basic compound, reduces the rate of hydrogenation while the previously mentioned acidic or neutral water-segregating agents, in considering only the pH effect, have either no effect or help the hydrogenation. Therefore, neutral or slightly acidic water-segregating agents will favor the hydrogenation rate. Although Raney nickel is ordinarily very basic, when washed with an organic solvent such as isopropanol to remove water, the pH becomes less basic.

The theoretical equivalent ratio of aldehyde or ketone to amine in the reaction is 1:1. However, in practice an excess of aldehyde or ketone is used and therefore it generally varies from 2 to 10:1, preferably from 5 to 10:1, most preferably from 6 to 8:1. When the lower ratios of aldehyde or ketone to amine are used a noticeable drop in tertiary amine production is observed. The higher ratios of aldehyde or ketone to amine have been noted to simply dilute the reaction mixture without a significant increase in yield.

The reaction is carried out under pressure at a temperature of from about 20° C. to 200° C., preferably from about 70° C. to 120° C. As the temperature is decreased the hydrogenation rate also decreases allowing by-product formation although the action of the water-segregating agent will be improved because of greater water retention. As the temperature is increased the hydrogenation rate generally increases minimizing by-product formation but often inhibiting the action of the water-segregating agent. It has also been observed that a higher temperature tends to significantly increase the rate of the undesirable aldolization reaction, and thus cause increased residue formation.

The reaction proceeds at a superatmospheric pressure, preferably from about 50 psig to 3000 psig. A greater hydrogenation pressure will not hinder the reaction unless the rate of the hydrogenation of the carbonyl group to an alcohol is significantly affected and becomes the predominate reaction. Lower hydrogenation pressures result in slower hydrogenation rates and increased by-product formation.

It was observed that the time required for the complete cessation of the hydrogen absorption in the laboratory experiments at the preferred conditions was usually about six hours. The time required in a particular reaction will vary and is dependent upon the specific reactants, catalyst, temperature and pressure used, as well as the size of the batch, as is known to those skilled in the art. The hydrogenation may be terminated prior to the cessation of hydrogen absorption although this leads to a lesser yield of product tertiary amine.

Addition of aldehyde or ketone to the reaction mixture in the reactor can be done directly at the start of the reaction or by feeding during the course of the reaction. Mixing of the reactants to obtain good solid-liquid-gas contact can be accomplished by either a high speed agitator or by a rocking motion of the high-pressure hydrogenation reactor.

If desired one can also have present in the reaction mixture an inert organic solvent, such as, methanol, ethanol, isopropanol and the like. It is advisable that the solvent be of low molecular weight to facilitate removal from the product of the reaction.

In a typical embodiment, bis(3-hydroxypropyl)amine is mixed in a pressure reactor, with acetone, Raney nickel, which has been previously washed three times with anhydrous isopropanol, and Type A molecular sieves, which have been previously dried at 350° C. The reactor is purged three times slowly at a pressure of 50 psig with hydrogen gas. The reactor is then pressurized to 1000 psig with hydrogen gas and heated to a temperature of about 80° C. Hydrogen gas is continually pumped into the reactor to keep the pressure at about 1000 psig as the reaction proceeds, and the reaction is continued until hydrogen absorption ceases. Isolation of the product, N-isopropylbis(3-hydroxypropyl)amine, is carried out by separation of the product by filtration from the catalyst mixture, followed by removal of the low-boiling alcohols, and then by simple distillation procedures well known to those skilled in the art.

Illustrative of the tertiary amines which can be produced by the process of this invention one can mention triethylamine, methyl isopropyl hexylamine, isopropylbis(3-hydroxypropyl)amine, dibutylethylamine, tributylamine and dimethylcyclohexyl methylamine.

It was completely unexpected and unobvious to find that the introduction of certain water-segregating agents in the reductive alkylation of a secondary amine with an aldehyde or ketone would result in such improved yields of product tertiary amine together with minimal formation of tarry residues and by-products.

The tertiary amines are known compounds having established utility. Thus, for example, the N-alkylbis(3-hydroxypropyl)amines have been shown to be effective modifiers of the dyeing of polyester fibers. Certain of the other tertiary amines produced by the process of this invention are converted into polyesters for melt-blending with polyethylene terephthalate resins as dyeability modifiers, as disclosed and claimed in U.S. Pat. No. 3,880,230. The novel process of this invention is also of advantage to the pharmaceutical industry in that it will facilitate the chemical reactions and synthesis of amine compounds with large ring systems, such as the steroids. In addition the laboratory synthesis of alkaloids, which contain the amine group, may also benefit by use of this novel process.

Experiments A to C are presented for comparative purposes using heretofore known procedures.

EXPERIMENT A

There were charged to a pressure reactor 26.6 grams of bis(3-hydroxypropyl)amine, 11.6 grams of acetone, 3.5 grams of Raney nickel catalyst and 35 ml of methanol. The reactor was purged with dry hydrogen three times at 50 psig, and then pressurized to 1000 psig and heated to 78° C. to 82° C. The pressure was maintained at 500 to 1000 psig by continuous addition of hydrogen gas for six hours at 75° C. to 85° C. while continuously agitating the mixture. When hydrogen absorption ceased, the reactor was cooled, the pressure was released and the reactor contents were removed and filtered. The filtered crude reaction product was then distilled at about 100° C. and a pressure of about 75 mm to remove low boiling alcohols used as solvent or formed by the hydrogenation of the acetone. The stripped product was then analyzed by gas-liquid chromatography with the column operating isothermally at 175° C. The analysis indicated a conversion to the desired tertiary amine, N-isopropylbis(3-hydroxypropyl)amine of only about 11 percent based on the secondary amine charged. An unidentified impurity eluting on the gas-liquid chromatograph between the two amines amounted to 2.5 percent by weight while the unreacted secondary amine amounted to about 84 weight percent of the unrefined reaction product.

EXPERIMENT B

There were charged to a pressure reactor 26.6 grams of bis(3-hydroxypropyl)amine, 81.3 grams of acetone and 5 grams of Raney nickel catalyst. The reaction was carried out and the crude hydrogenation product was isolated and analyzed in a manner similar to that described in Experiment A. Gas-liquid chromatographic analysis indicated a conversion to the desired tertiary amine, N-isopropylbis(3-hydroxypropyl)amine, of only about 53 percent based on the secondary amine charged. Increasing the acetone content in the reaction improved the conversion to the tertiary amine but a significant amount of secondary amine still remained to cause a separation problem and impurities were present in a significantly higher concentration of 8 percent by weight.

The crude reaction product was extracted in a separatory funnel using 300 ml of a 50/50 water/chloroform mixture. The chloroform layer selectively removed most of the tertiary amine product while 12.4 grams of the unreacted secondary amine, 2.7 grams of the impurities and 7.3 grams of the tertiary amine were left in the aqueous layer. Simple distillation at a pressure of about 0.01 mm Hg, a head temperature of from 90° C. to 100° C. and a kettle temperature of from 110° C. to 150° C., of the chloroform layer yielded 11.2 grams of the desired tertiary amine, N-isopropylbis(3-hydroxypropyl)amine having a refractive index at 20° C. of 1.4659. Infrared and nuclear magnetic spectra further confirmed the structure.

EXPERIMENT C

There were charged to a pressure reactor 26.6 grams of bis(3-hydroxypropyl)amine, 81.3 grams of acetone, 5 grams of Raney nickel catalyst and 18.4 grams of potassium carbonate. The reaction was carried out and the crude hydrogenation product was isolated and analyzed in a manner similar to that described in Experiment A except that the hydrogenation time was extended to twelve hours. Gas-liquid chromatographic analysis indicated a conversion to the desired tertiary amine, N-isopropylbis(3-hydroxypropyl)amine, of only about 8 percent based on the secondary amine charged. The impurity eluting on the gas-liquid chromatograph between the two amines amounted to 37 weight percent of the stripped crude reaction product. This experiment shows that potassium carbonate cannot be considered a water-segregating agent.

The following examples serve to further illustrate the invention.

EXAMPLE 1

There were charged to a pressure reactor 26.6 grams of bis(3-hydroxypropyl)amine, 81.3 grams of acetone, 5 grams of Raney nickel catalyst and 20 grams of Type A zeolitic molecular sieves. The reaction was carried out and the crude hydrogenation product was isolated and analyzed in a manner similar to those described in Experiment A. Gas-liquid chromatographic analysis indicated a conversion to the desired tertiary amine, N-isopropylbis(3-hydroxypropyl)amine, of about 95 percent based on the secondary amine charged. In this example there was no evidence of the impurities normally produced in an experiment in which the water-segregating agent is not present.

The tertiary amine produced was recovered from the crude using the same water/chloroform extraction procedure used in Experiment B. The chloroform was removed and the residue was simply distilled; a total of 25.8 grams of the purified N-isopropylbis(3-hydroxypropyl)amine was recovered having a refractive index at 20° C. of 1.4663. Infrared and nuclear magnetic resonance spectra further confirmed the structure.

EXAMPLE 2

There were charged to a pressure reactor 26.6 grams of bis(3-hydroxypropyl)amine, 81.3 grams of acetone, 5 grams of Raney nickel catalyst and 20 grams of Type A zeolitic molecular sieves. The reaction was carried out and the crude hydrogenation product was isolated and analyzed in a manner similar to that described in Experiment A. Gas-liquid chromatographic analysis indicated a conversion to the desired tertiary amine, N-isopropylbis(3-hydroxypropyl)amine, of about 97 percent based on the secondary amine charged. A trace of impurities was seen in the crude product.

The tertiary amine was recovered by simple distillation at 0.05 mm Hg with a head temperature of from 115° C. to 125° C. and a kettle temperature of from 135° C. to 190° C. A total of 33 grams of the refined N-isopropylbis(3-hydroxypropyl)amine was obtained having a refractive index at 20° C. of 1.4665. Essentially no forefraction or residue was isolated during the distillation. Infrared and nuclear magnetic resonance spectra further confirmed the structure.

In a similar manner the above reaction is carried out using a nickel-on-kieselguhr as the hydrogenation catalyst.

EXAMPLE 3

There were charged to a pressure reactor 26.6 grams of bis(3-hydroxypropyl)amine, 81.3 grams of acetone, 5 grams of Raney nickel catalyst and 5 grams of Type A zeolitic molecular sieves. The reaction was carried out and the crude hydrogenation product was isolated and analyzed in a manner similar to that described in Experiment A. Gas-liquid chromatographic analysis indicated a conversion to the desired tertiary amine, N-isopropylbis(3-hydroxypropyl)amine, of about 73 percent based on the secondary amine charged. The reduction in the molecular sieve content as water-segregating agent appreciably decreased the conversion of secondary amine to tertiary amine and resulted in the formation of more impurities than obtained in Example 2, amounting to 2.3 weight percent of the crude hydrogenation product.

EXAMPLE 4

There were charged to a pressure reactor 26.6 grams of bis(3-hydroxypropyl)amine, 81.3 grams of acetone, 5 grams of Raney nickel catalyst and 20 grams of Type A zeolitic molecular sieves. The reaction was carried out and the crude hydrogenation product was isolated and analyzed in a manner similar to that described in Experiment A except that the hydrogenation pressure was reduced to 150 psig and the hydrogenation time was extended to twelve hours. Gas-liquid chromatographic analysis indicated a conversion to the desired tertiary amine, N-isopropylbis(3-hydroxypropyl)amine, of about 89 percent based on the secondary amine charged. The lowering of the hydrogenation pressure significantly increased the amount of impurities formed in the crude reaction product to 6 percent by weight. Attempts to identify the impurities were unsuccessful, although analysis by mass spectrometry revealed molecules containing two nitrogen atoms to one hydroxyl group and three carbon linkages, and molecular weights ranging from 117 to 158.

EXAMPLE 5

There were charged to a pressure reactor 26.6 grams of bis(3-hydroxypropyl)amine, 27 grams of acetone, 2.7 grams of Raney nickel catalyst and 20 grams of Type A zeolitic molecular sieves. The reaction was carried out and the crude hydrogenation product was isolated and analyzed in a manner similar to that described in Experiment A. Gas-liquid chromatographic analysis indicated a conversion to the desired tertiary amine, N-isopropylbis(3-hydroxypropyl)amine, of about 69 percent based on the secondary amine charged. The unidentified impurity amounted to 2.1 weight percent of the stripped unrefined reaction product.

EXAMPLE 6

There were charged to a pressure reactor 17.4 grams of methyl-secondary-butylamine, 81.3 grams of acetone, 5 grams of Raney nickel catalyst and 20 grams of Type A zeolitic molecular sieves. The reaction was carried out and the crude hydrogenation product was isolated and analyzed in a manner similar to that described in Experiment A except that the column used in the gas-liquid chromatographic analysis was programmed to heat at a rate of 15° C. per minute from 100° C. to 200° C. Gas-liquid chromatographic analysis indicated a conversion to the desired tertiary amine, methylisopropyl-secondary-butylamine of about 14 percent based on the secondary amine charged. This example illustrates that more sterically hindered starting secondary amines are more difficult to convert to the tertiary amines.

In a similar manner, the above reaction is carried out using palladium-on-carbon, platinum-on-clay or ruthenium-on-silica as the hydrogenation catalyst.

For purposes of comparison the above experiment was repeated except that no molecular sieves were added to the reaction mixture as water-segregating agents. Gas-liquid chromatographic analysis indicated a conversion to the desired tertiary amine, methylisopropyl-secondary-butylamine of only 1.1 percent based on the secondary amine charged. This indicates that the use of the water-segregating agent increased the conversion 13 fold.

EXAMPLE 7

There were charged to a pressure reactor 26.6 grams of bis(3-hydroxypropyl)amine, 81.3 grams of acetone, 5 grams of Raney nickel catalyst and 12 grams of calcium chloride. The reaction was carried out and the crude hydrogenation product was isolated and analyzed in a manner similar to that described in Experiment A except that the hydrogenation time was extended to twelve hours. Gas-liquid chromatographic analysis indicated a conversion to the desired tertiary amine, N-isopropylbis(3-hydroxypropyl)amine of greater than 99 percent based on the secondary amine charged. There was no evidence of the major impurity observed in Experiment A.

EXAMPLE 8

There were charged to a pressure reactor 26.6 grams of bis(3-hydroxypropyl)amine, 81.3 grams of acetone, 5 grams of Raney nickel catalyst and 1 gram of calcium chloride. The reaction was carried out and the crude hydrogenation product was isolated and analyzed in a manner similar to that described in Experiment A except that the hydrogenation time was extended to eight hours. Gas-liquid-chromatographic analysis indicated a conversion to the desired tertiary amine, N-isopropylbis(3-hydroxypropyl)amine of about 97 percent based on the secondary amine charged. There was no evidence of impurities.

The reaction product was isolated in a manner similar to that described in Example 2. A total of 32 grams of the refined N-isopropylbis(3-hydroxypropyl)amine was isolated having a refractive index at 20° C. of 1.4670. Essentially no forefraction or residue was isolated during the distillation. Infrared and nuclear magnetic resonance spectra further confirmed the structure and high purity of the product tertiary amine.

EXAMPLE 9

There were charged to a pressure reactor 26.6 grams of bis(3-hydroxypropyl)amine, 81.3 grams of acetone, 5 grams of Raney nickel catalyst and 0.1 gram of calcium chloride. The reaction was carried out and the crude hydrogenation product was isolated and analyzed in a manner similar to that described in Experiment A except that the hydrogenation time was extended to eight hours. Gas-liquid chromatographic analysis indicated a conversion to the desired tertiary amine, N-isopropyl-bis(3-hydroxypropyl)amine, of about 93 percent based on the secondary amine charged. Traces of impurities were seen in gas-liquid chromatographic analysis of the unrefined product.

EXAMPLE 10

There were charged to a pressure reactor 26.6 grams of bis(3-hydroxypropyl)amine, 81.3 grams of acetone, 5 grams of Raney nickel catalyst and 3.5 grams of magnesium sulfate. The reaction was carried out and the crude hydrogenation product was isolated and analyzed in a manner similar to that described in Experiment A. Gas-liquid chromatographic analysis indicated a conversion to the desired tertiary amine, N-isopropylbis(3-hydroxypropyl)amine, of about 91 percent based on the secondary amine charged. The impurity eluting on the gas-liquid chromatograph between the two amines amounted to only 1.3 percent by weight of the stripped crude reaction product.

The reaction product was refined using the procedures described in Example 2. A total of 30 grams of the refined N-isopropylbis(3-hydroxypropyl)amine was isolated having a refractive index at 20° C. of 1.4698. Essentially no forefraction or residue was isolated during the distillation. Nuclear magnetic resonance spectra further confirmed the structure and high purity of the product tertiary amine.

In a similar manner, the above reaction is carried out using rhodium-on-carbon as the hydrogenation catalyst.

EXAMPLE 11

There were charged to a pressure reactor 26.6 grams of bis(3-hydroxypropyl)amine, 81.3 grams of acetone, 5 grams of Raney nickel catalyst and 4.1 grams of sodium sulfate. The reaction was carried out and the crude hydrogenation product was isolated and analyzed in a manner similar to that described in Experiment A except that the hydrogenation time was extended to nine hours. Gas-liquid chromatographic analysis indicated a conversion to the desired tertiary amine, N-isopropyl-bis(3-hydroxypropyl)amine, of about 89 percent based on the secondary amine charged. The impurity eluting on the gas-liquid chromatograph between the two amines amounted to only 1.9 weight percent of the stripped unrefined reaction product.

In a similar manner, the above reaction is carried out using osmium-on-clay as the hydrogenation catalyst.

EXAMPLE 12

There were charged to a pressure reactor 26.6 grams of bis(3-hydroxypropyl)amine, 81.3 grams of acetone, 5 grams of Raney nickel catalyst and 13.6 grams of calcium sulfate. The reaction was carried out and the crude hydrogenation product was isolated and analyzed in a manner similar to that described in Experiment A. Gas-liquid chromatographic analysis indicated a conversion to the desired tertiary amine, N-isopropylbis(3-hydroxypropyl)amine, of about 91 percent based on the secondary amine charged. The impurity eluting on the gas-liquid chromatograph between the two amines amounted to only 1.0 weight percent of the stripped unrefined reaction product.

In a similar manner, the above reaction is carried out using iridium-on-silica as the hydrogenation catalyst.

What is claimed is:

1. A process for the production of tertiary amines of the formula

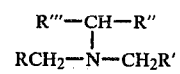

which comprises the reductive alkylation at from 20° C. to 200° C. of (I) a secondary amine of the formula

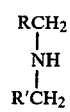

with (II) a member from the group of the aliphatic aldehydes and the aliphatic ketones of the formula

where R and R' can be:
(a) alkyl, substituted or unsubstituted, linear or branched, having from one to twenty carbon atoms;
or (b) a substituted or unsubstituted cycloalkyl having from four to eight ring carbon atoms;
or (c) a substituted or unsubstituted hydroxyalkyl, linear or branched, having from one to twenty carbon atoms;
or (d) a substituted or unsubstituted aralkyl having from seven to twenty carbon atoms;
or (e) hydrogen;
and R" and R'" singly can be:
(a) alkyl, substituted or unsubstituted, linear or branched, having from one to twenty carbon atoms;
or (b) hydrogen;
or (c) when taken together they can be alkylene having from three to six carbon atoms forming a cyclic ketone, in contact with hydrogen at a superatmospheric pressure, a water-segregating agent and a catalytically effective amount, sufficient to carry out the reductive alkylation, of a hydrogenation catalyst.

2. A process as claimed in claim 1 wherein said water-segregating agent is a zeolitic molecular sieve having a pore diameter of from 2.5 to 5 Angstrom units.

3. A process as claimed in claim 2 wherein said molecular sieve is a Type A molecular sieve.

4. A process as claimed in claim 1 wherein said water-segregating agent is calcium chloride.

5. A process as claimed in claim 1 wherein said water-segregating agent is magnesium sulfate.

6. A process as claimed in claim 1 wherein said water-segregating agent is calcium sulfate.

7. A process as claimed in claim 1 wherein said water-segregating agent is sodium sulfate.

8. A process as claimed in claim 1 wherein said hydrogenation catalyst is Raney nickel.

9. A process as claimed in claim 1 wherein the reaction is carried out at a temperature of from 70° C. to 120° C.

10. A process as claimed in claim 1 wherein the reaction is carried out at a pressure of from 50 psig to 3000 psig.

11. A process as claimed in claim 1 wherein said catalyst is present at a concentration of from 0.5 weight percent to 10 weight percent based on the total weight of the aldehyde or ketone, secondary amine, and water-segregating agent charged.

12. A process as claimed in claim 1 wherein the mole ratio of component (II) to component (I) is from 2 to 10:1.

13. A process as claimed in claim 1 wherein the mole ratio of component (II) to component (I) is from 5 to 10:1.

14. A process as claimed in claim 1 wherein the mole ratio of component (II) to component (I) is from 6 to 8:1.

15. A process as claimed in claim 1 wherein the concentration of said water-segregating agent ranges from 0.1 weight percent to 20 weight percent based on the total weight of aldehyde or ketone, secondary amine, and catalyst charged.

* * * * *